US008821858B2

(12) United States Patent
Gandy et al.

(10) Patent No.: US 8,821,858 B2
(45) Date of Patent: Sep. 2, 2014

(54) LYOPHILIZED PLATELET RICH PLASMA FOR THE USE IN WOUND HEALING (CHRONIC OR ACUTE) AND BONE OR TISSUE GRAFTS OR REPAIR

(75) Inventors: James Bennie Gandy, Calhoun, LA (US); Mackie J. Walker, Jr., Aiken, SC (US)

(73) Assignee: GW IP, LLC, Shreveport, LA (US)

( * ) Notice: Subject to any disclaimer, the term of this patent is extended or adjusted under 35 U.S.C. 154(b) by 1324 days.

(21) Appl. No.: 12/079,356

(22) Filed: Mar. 26, 2008

(65) Prior Publication Data

US 2008/0213238 A1 Sep. 4, 2008

Related U.S. Application Data

(63) Continuation of application No. 11/054,400, filed on Feb. 9, 2005, now abandoned.

(51) Int. Cl.
| | | |
|---|---|---|
| *A01N 63/00* | (2006.01) | |
| *A61K 35/14* | (2006.01) | |
| *A61K 38/18* | (2006.01) | |
| *C07K 14/475* | (2006.01) | |
| *C07K 14/49* | (2006.01) | |
| *C12P 21/04* | (2006.01) | |
| *A61K 35/16* | (2006.01) | |
| *A61K 38/48* | (2006.01) | |

(52) U.S. Cl.
CPC ............... *A61K 35/19* (2013.01); *A61K 35/16* (2013.01); *A61K 38/4833* (2013.01)
USPC .......... 424/93.72; 424/532; 514/7.6; 514/8.2; 435/70.4

(58) Field of Classification Search
None
See application file for complete search history.

(56) References Cited

U.S. PATENT DOCUMENTS

| | | | |
|---|---|---|---|
| 4,056,484 A | 11/1977 | Heimburger et al. | |
| 4,350,687 A | 9/1982 | Lipton et al. | |
| 4,957,742 A | 9/1990 | Knighton | |
| 5,165,938 A | 11/1992 | Knighton | |
| 5,185,160 A | 2/1993 | Chao | |
| 5,332,578 A | 7/1994 | Chao | |
| 5,378,461 A | 1/1995 | Neigut | |
| 5,470,831 A | 11/1995 | Whitman et al. | |
| 5,599,558 A | 2/1997 | Gordinier et al. | |
| 5,651,966 A | 7/1997 | Read et al. | |
| 5,776,892 A | 7/1998 | Counts et al. | |
| 5,993,804 A | 11/1999 | Read et al. | |
| 6,303,112 B1 | 10/2001 | Worden | |
| 6,524,568 B2 | 2/2003 | Worden | |
| 6,706,687 B1 | 3/2004 | Eriksson et al. | |
| 2001/0019819 A1* | 9/2001 | Wolkers et al. | 435/2 |
| 2002/0114775 A1 | 8/2002 | Pathak | |
| 2003/0152639 A1 | 8/2003 | Britton et al. | |
| 2004/0001816 A1 | 1/2004 | Worden | |
| 2004/0197319 A1 | 10/2004 | Harch et al. | |
| 2004/0265293 A1 | 12/2004 | Crowe | |

FOREIGN PATENT DOCUMENTS

| | | | | |
|---|---|---|---|---|
| WO | WO 95/15763 | * | 6/1995 | ............. A61K 35/14 |
| WO | WO 97/34614 | * | 9/1997 | ............. A61K 35/14 |

OTHER PUBLICATIONS

Answers.com "lyophilize" 2pgs, accessed Apr. 22, 2011 at http://www.answers.com/topic/lyophilize.*
Merriam Webster Online "lyophilize" 1 pg, accessed Apr. 22, 2011 at http://www.merriam-webster.com/dictionary/lyophilize.*
Cardigan et al. "The quality of platelets after storage for 7 days" Transfusion Medicine, 2003, 13, 173-187.*
Robert J. Brant, Declaration Under 37 CRF 1.132 from case 12/459911 signed Jan. 8, 2013, 15 pages.*
PCT Int'l Search Report, Jul. 2, 2007.
Van der Meulen, et al., Isolation and Partial Characterization of Platelet alpha.-Granule Membranes, J. Membrane Biol. 71, 47-59 (1983).
Chao, et al., Infusible Platelet Membrane Microvesicles: Potential Transfusion Substitute for Platelets, Transfusion, 36:536-542 (1996).
Gogstad, A Method for the Isolation of .alpha.-Granules From Human Platelets, Thrombosis Research, 20:669-681 (1980).
Hernandez, In Vitro Evaluation of the Hemostatic Effectiveness of Non Viable Platelet Preparations: Studies with Frozen-Thawed, Sonicated or Lyophilized Platelets, Vox Sang 73: 36-42 (1997).
Fukami, Human Platelet Storage Organelles, Thrombos. Haemostas, (Stuttg.), 38: 963-970 (1977).

* cited by examiner

*Primary Examiner* — Thane Underdahl
(74) *Attorney, Agent, or Firm* — McNair Law Firm, P.A.; Seann P. Lahey

(57) ABSTRACT

This invention relates to an improved Lyophilized platelet rich plasma used to make a platelet gel wound healant, and methods of preparation and use thereof for healing wounds are disclosed. The improved wound healant comprises therapeutically effective amounts of activated growth factors, platelet ghost, plasma (know as the plasma back bone), white blood cells with optional none, one or more additional antioxidant such as vitamin A and/or C and/or E, and/or none one or more antibiotics and/or GHK-Cu (produced by ProCyte Inc.)

11 Claims, No Drawings

LYOPHILIZED PLATELET RICH PLASMA FOR THE USE IN WOUND HEALING (CHRONIC OR ACUTE) AND BONE OR TISSUE GRAFTS OR REPAIR

This application is a continuation of U.S. patent application Ser. No. 11/054,400 filed Feb. 9, 2005, now abandoned and the benefit of all priority rights to and for that application are hereby claimed pursuant to 35 U.S.C. 120.

FIELD OF THE INVENTION

This application is based on Provisional application No. 60/542,903 Filed Feb. 9, 2004. The invention relates to an improved Lyophilized platelet rich plasma used to make a platelet gel wound healant, and methods of preparation and use thereof for healing wounds are disclosed. The improved wound healant comprises a therapeutically effective amount of activated growth factors with optional none, one or more additional anti-oxidant such as vitamin A and/or C and/or E, and/or one or more antibiotics and/or GHK-Cu (produced by ProCyte Inc.).

The present invention relates to improved Lyophilized platelet rich plasma for the use in wound healing and bone or tissue grafts and methods of making and use thereof of Lyophilized or fixed platelets.

The present invention generally relates to the therapeutic uses of blood platelets and fresh plasma that has been combined and lyophilized, and more particularly to manipulations or modifications of platelets and plasma, such as in preparing freeze-dried compositions that can be rehydrated at the time of application and which when rehydrated have a normal response to thrombin and other agonists with respect to that of fresh platelets. The inventive compositions are useful in applications such as wound care.

PRIOR EFFORT OF OTHERS

Several techniques for preservation of platelets have been developed over the past few decades. Cryopreservation of platelets using various agents, such as glycerol (Valeri et al., Blood, 43, 131-136, 1974) or dimethyl sulfoxide, "DMSO" (Bock et al., Transfusion, 35, 921-924, 1995), as the cryoprotectant has been done with some success. The best results have been obtained with DMSO. However, a considerable fraction of these cells are partly lysed after thawing and have the shape of a balloon. These balloon cells are not responsive to various agonists, so that overall responsiveness of frozen thawed platelets to various agonists is reduced to less than 35% compared with fresh platelets. The shelf life of cryopreserved DMSO platelets at −80.degree. C. is reported to be one year, but requires extensive washing and processing to remove cryoprotective agents, and even then the final product has a severe reduction in ability to form a clot.

Attempts to dry platelets by Lyophilization have been described with paraformaldehyde fixed platelets (Read et al., Proc. Natl. Acad Sci. USA, 92, 397-401, 1995). U.S. Pat. No. 5,902,608, issued May 11, 1999, inventors Read et al. describe and claim a surgical aid comprising a substrate on which fixed, dried blood platelets are carried. These dried blood platelets are fixed by contacting the platelets to a fixative such as formaldehyde, paraformaldehyde, gutaraldehyde, or permanganate. Proper functioning of lyophilized platelets that have been fixed by such fixative agents in hemostasis is questionable.

Spargo et al., U.S. Pat. No. 5,736,313, issued Apr. 7, 1998, has described a method in which platelets are loaded overnight with an agent, preferably glucose, and subsequently lyophilized. The platelets are preincubated in a preincubation buffer and then are loaded with carbohydrate, preferably glucose, having a concentration in the range of about 100 mM to about 1.5M. The incubation is taught to be conducted at about 10.degree. C. to about 37.degree. C., most preferably about 25.degree. C.

U.S. Pat. No. 5,827,741, Beattie et al., issued Oct. 27, 1998, discloses cryoprotectants for human platelets, such as dimethylsulfoxide and trehalose. The platelets may be suspended, for example, in a solution containing a cryoprotectant at a temperature of about 22.degree. C. and then cooled to below 15.degree. C. This incorporates some cryoprotectant into the cells.

Other workers have sought to load platelets with trehalose through use of electroporation before drying under vacuum. However, electroporation is very damaging to the cell membranes and is believed to activate the platelets. Activated platelets have dubious clinical value.

Accordingly, a need exists for the effective and efficient preservation of platelets such that they maintain, or preserve, their biological properties, particularly their response to platelet agonists such as thrombin, and which they release their growth factors. Further, it would also be useful to expand the types of present vehicles that are useful for wound care.

There have been many different substances and methods developed in the past for treating wounds, depending upon the type and location and severity of the wound. A wound is generally defined as an injury to an area of the body of a human or animal. Although injury to the surface of the skin is the most well known type of wound, the surfaces of internal organs may also be wounded, such as during surgery, rupture of the spleen or liver, or resulting from traumatic blows to the body surface in the vicinity of an internal organ.

Medical practice characterizes wounds as chronic or acute, according to the persistence and severity of the wound. A chronic wound is one that is prolonged or lingering, rather than promptly healed. An acute wound is one that occurs relatively quickly, and heals relatively quickly as well. Tissue wounds may have a wide spectrum of manifestations, as small as merely an abnormal microscopic tear or fissure in tissue (or a surface thereof), or as large as the abrasion or ablation of the skin covering a substantial portion of the body, such as in a burn victim. Acute wounds covering a large or movable surface are usually the most difficult to guard from infection, and to heal.

Blood and bodily fluids include various substances that affect wound healing. The blood is the primary medium for delivering healing agents to the wound site, and for transporting foreign or harmful substances away from the wound. Whole blood is primarily comprised of three main types of cells suspended in a protein rich solution known as plasma. The three main cell types in whole blood are erythrocytes (a.k.a. red blood cells), leukocytes (a.k.a. white blood cells) and thrombocytes (a.k.a. platelets). The red blood cells are the iron-containing cells that facilitate the transport and transfer of oxygen to body tissue, and the removal of carbon dioxide. The white blood cells perform a variety of functions such as phagocytosis of foreign bodies and production of antibodies, and are primarily responsible for fighting infection and foreign substances within the blood or wound site. Platelets perform many functions such as plugging leaks in blood vessels and helping begin the process leading to the formation of a blood clot; platelets contain substances known as growth factors that facilitate the formation of new tissue.

Although there are several methods for separating whole blood into its various components, one of the most convenient and expeditious methods is accomplished by differentially centrifuging blood or some of its components (i.e., apheresis). Using apheresis, the red and white blood cells and plasma may be separated out and returned to the donor's or patient's body, leaving the sequestered platelets in essentially concentrated form for use in wound healing techniques. This may be preformed at a blood collection center, blood bank, at the Physicians Clinic or Hospital. From blood extracted from a patient or from the other forms of collection methods, the platelets may thus be obtained and activated for use on the patient; methods of using a patient's own blood are called "autologous" or "autogenic" donor methods. Another method using blood donated by one or more third parties for use by a patient are called "homologous" or "heterologous" donor methods, or collectively called "allogenic" methods.

One of the proteins suspended in plasma is fibrinogen, which reacts with substances released into (or attracted by) wound sites to produce sticky strands of fibrin. Such reactions result in the cross linking of the fibrin strands to form a mesh that holds and supports the deposit or growth of other tissue materials at the wound site. Therefore, the need for fresh plasma also known in the art "The Plasma Back Bone".

The wound healing process is generally considered to occur in several stages, generally known as the healing cascade. After tissue injury, platelets are among the first cells to appear in the vicinity of the wound. Activation of a platelet by an agonist such as thrombin, or other agonists such as those listed elsewhere herein, leads to the release of granule material from within the platelet. Such granulation activation results in the release of proteins known as growth factors, primarily concentrated in the alpha granules of platelets. These released growth factors stimulate the formation of new tissue; when applied to wounds, growth factors have been known to increase the rate of collagen laydown, vascular ingrowth, fibroblast proliferation and overall healing. The release of a protein known as platelet-derived growth factor (PDGF) is a chemotactic signal for monocytes, neutrophils and fibroblasts, which then move into the wound, to begin the inflammatory stage of the healing process. During this time, monocytes secrete a number of factors including PDGF and transforming growth factor-.beta.1 (also found in platelets), which recruits and activates fibroblasts, to begin the repair stage of the healing process. Subsequently, wound healing continues through the process of collagen remodeling within the wound. Thus the importance of the ability of the Lyophilized platelet rich plasma to release their growth factors.

Based upon the foregoing general scientific principles, already known in the field are wound sealants made from biological materials obtained primarily from tissue other than blood platelets. An example is wound sealants such as "fibrin glue", which often are essentially a mixture of co-coagulants (thrombin and calcium), concentrated fibrinogen and other coagulation proteins. In most applications, the primary roles of fibrin glue are to seal wound surfaces to prevent loss of blood and other body fluids after surgery, and to provide adhesion between adjacent tissue surfaces. These products form a hard, cast-like covering over the area to be sealed, and tend to be non-yielding to limb movement.

While there has been much research concerning fibrin glue, this material belongs to a separate field from the present invention, primarily because fibrin glues typically contain cryoprecipitated proteins without platelets. The use of fibrin glue is discussed extensively in the scientific literature; for example, see the references cited in U.S. Pat. No. 5,585,007 issued to Antanavich et al on Dec. 17, 1996.

Wound treatment compositions derived from platelet enriched concentrates are known and possess certain advantages over materials without platelets such as fibrin glue. One reason is that natural wound healing agents are released by the platelets. Further, the concentration of platelets likewise allows for a concentrated amount of wound healing factors. Representative examples of platelet derived wound treatment compositions are described for instance in Hood U.S. Pat. No. 5,733,545; Knighton U.S. Pat. No. 5,165,938; and Gordiner U.S. Pat. No. 5,599,558. This form of treatment has major problems, like time consuming and problems collecting blood sometimes with expensive machines and disposables.

Platelet concentrates are typically isolated by the process of differential centrifugation, which essentially allows separating the blood into at least three different components: packed erythrocytes (red blood cells), plasma and platelet concentrate. Platelet concentrate can be combined with a solution of either sodium or calcium mixed with thrombin ("calcified thrombin"), which instantaneously form a composition of activated platelets that, when made with the necessary viscosity, can be utilized as a wound sealant. The chemical reactions and cascades that normally occur when thrombin is added to the concentrated platelets are indeed complex. See, for instance, Reeder, et al, in Proceedings of the American Academy of Cardiovascular Perfusion, Vol. 14, January 1993. Such wound sealants typically set up into a hard mass covering the application site, thereby sealing the site against further blood loss and external contaminants.

There are a number of disadvantages associated with conventional wound compositions derived from platelet concentrates. For instance, activation of platelets leads to instantaneous hardening of the material and thus requires the physician to both activate and apply the platelet composition to the wound site within seconds of activation. Also, certain platelet compositions must be applied to the wound site on a daily basis and thus require regular blood withdrawal from the patient. This is time consuming and if more of the compositions is needed, then another needle stick is needed and the process time required to make the composition.

Accordingly, an improved Lyophilized platelet enriched plasma wound treatment composition which avoids or diminishes the problems associated with typical platelet enriched wound compositions and would be desirable.

SUMMARY OF THE INVENTION

In one aspect of the present invention, a dehydrated composition is provided comprising freeze-dried platelets and fresh plasma that are effectively to preserve biological properties during freeze drying and rehydration. These platelets are rehydratable so as to have a normal response to at least one agonist, such as thrombin. For example, substantially all freeze-dried platelets of the invention when rehydrated and mixed with thrombin (1 U/ml) form a clot within three minutes at 37.degree. C. The dehydrated composition can include one or more other agents, such as antibiotics, antifungals, growth factors, or the like, depending upon the desired therapeutic application.

The present invention relates to an improved Lyophilized platelet and plasma composition for wound treatment, a method of making and use thereof. The composition comprises Lyophilized platelets and plasma composition in liquid form to the wound site and will gel to prevent the material from flowing away from the site. Optional antibiotics may be included in the improved composition to prevent infections at the wound site. The presence of the anti-oxidant, including vitamins and non-vitamin anti-oxidants, and other healing promotion materials that do not detract from, substantially interfere with, or even destroy the different thrombin activation reactions. The inventive Lyophilized platelet gels containing fresh plasma is prepared for topical application at the wound site and avoid the requirement for daily reapplication.

Methods of making and using inventive embodiments are also described. One such method is a process of preparing a dehydrated composition comprising providing a source of platelets and fresh plasma and lyophilizing the platelets and plasma. The rehydration preferably done with de-ionized water.

While the inventive composition is preferably used for topical application to the exterior surface of the chronic wounds such as ulcers of the feet of diabetics, the composition may be applied to facilitate the healing of other wounds such as acute wounds such as surgery burns. However, the composition of matter and the methods described herein are not limited solely to topical application.

The inventive composition increases the amount of growth factors in the wound, and thereby facilitates the promotion of the healing rate. This may be especially important in "wounded" patients, especially those with chronic wounds who may lack sufficient circulation to facilitate the healing cascade. The invention described herein also facilitates the covering of the wound area with a substance that prevents or helps to reduce infection caused by most bacteria;

Practice of the invention permits the manipulation or modification of platelets and plasma while maintaining, or preserving, biological properties, such as a response to thrombin. The inventive freeze-dried platelets and plasma including the freeze-dried platelets, are substantially shelf stable at ambient temperatures when packaged in moisture barrier materials.

In most general terms, the invention described herein expands the uses for concentrated platelet materials, especially those in gel form, by improving the speed and convenience of making the composition; the invention described herein also improves the performance of the concentrated platelet composition, by making it more useable for applications over longer periods of time, and by enhancing the wound healing and infection fighting properties.

Another aspect of the present invention involves adding one or more antibiotic substance at one or more times during the processing period so that the resulting concentrated platelet and plasma composition contains either one or a variety of the antibiotics. The use of an antibiotic in concentrated platelet and plasma compositions that enhances the complex healing cascade is indeed novel. The invention disclosed herein involves adding such substances in a manner that does not detract from, substantially interfere with, or even destroy these different reactions, pH balances and potency.

Another aspect of the present invention involves adding one or more vitamins, to the concentrated platelet gel. Vitamins are known to have wound healing and anti-oxidant properties. Representative examples of suitable, but none limiting, vitamins include vitamin E, vitamin A, vitamin C and other retinoids.

In yet another aspect of the invention, non-vitamin anti-oxidants may be included in the concentrated platelet gel. Non-limiting representative examples of such anti-oxidants include beta-carotene.

DETAILED DESCRIPTION OF THE INVENTION

For the sake of simplicity and to give the claims of this patent application the broadest interpretation and construction possible, the following definitions will apply:

(a) The phrase blood collecting or blood extraction (or similar phrase) includes techniques, materials and apparatus known in the field, such as (for example) inclusion of anticoagulation materials, the use of blood drawing and infusion apparatus.

(b) the phrase growth factor means any material(s) promoting growth of a tissue.

(c) The term thrombin may include calcified thrombin, in particular, about 5,000 units of thrombin per 5 ml of 10% of aqueous calcium chloride solution; it may include calcified bovine thrombin as well as autologous thrombin, allogeneic thrombin or recombinant human thrombin.

(d) The term viscosity means those characteristics of the specified material(s) determining the degree of gelation, such as (for example) the firmness or hardness of the material, or the degree to which the material resists flowing like a fluid.

(e) The term therapeutically effective amount means the amount or amounts of the constituent elements or combination thereof necessary to enhance wound healing such as, for example, the reduction in the volume or surface area of a wound, the increase in the amount of granulation tissue or other biological material facilitating collagen laydown, vascular ingrowth, fibroblast proliferation or overall healing; all of the versions of the invention described herein are assumed to have the therapeutically effect amount(s) of constituent substances, or combinations thereof.

(f) the term anti-oxidant refers to any material(s) having anti-oxidant properties. Anti-oxidant would include, without limitation, vitamins such as vitamins C, A and E and non-vitamins such as -carotene.

Also for the sake of simplicity, the conjunctive "and" may also be taken to include the disjunctive "or", and vice versa, whenever necessary to give the claims of this patent application the broadest interpretation and construction possible. Likewise, when the plural form is used it may be taken to include the singular form and vice versa.

In most general terms, the invention includes a wound healant composition comprising activated growth factors and ascorbic acid. In the prevalent version of the invention, said growth factors are included within platelets. The body produces many substances generally known as growth factors, and these growth factors are contemplated for use in the present invention. The preferred growth factors for use in the present invention are selected from the group consisting of platelet-derived growth factor (PDGF), platelet-derived angiogenesis factor (PDAF), vascular endotheial growth factor (VEGF), platelet-derived epidermal growth factor (PDEGF), platelet factor 4 (PF-4), transforming growth factor .beta. (TGF-B), acidic fibroblast growth factor (FGF-A), basic fibroblast growth factor (FGF-B), transforming growth factor .alpha. (TGF-A), insulin-like growth factors 1 and 2 (IGF-1 and IGF-2), .beta. thromboglobulin-related proteins (BTG), thrombospondin (TSP), fibronectin, von Wallinbrand's factor (vWF), fibropeptide A, fibrinogen, albumin, plasminogen activator inhibitor 1 (PAI-1), osteonectin, regulated upon activation normal T cell expressed and presumably secreted (RANTES), gro-.alpha., vitronectin, fibrin D-dimer, factor V, antithrombin III, immunoglobulin-G (IgG), immunoglobulin-M (IgM), immunoglobulin-A (IgA), a2-macroglobulin, angiogenin, Fg-D, elastase, keratinocyte growth factor (KGF), epidermal growth factor (EGF), fibroblast growth factor (FGF), tumor necrosis factor (TNF), fibroblast growth factor (FGF) and interleukin-1 (IL-1), Keratinocyte Growth Factor-2 (KGF-2), and combinations thereof One of the important characteristics common to each substance, supporting the inclusion of each in this particular group, is that each such substance is known or believed to enhance cell or tissue growth. Moreover, said substances, or various combinations thereof, are known or believed to function together in an unexpected synergistic manner to promote wound healing. Suitable, non-limiting, anti-oxidants useful in the invention include but are not limited to vitamins such as vitamin C (ascorbic acid), vitamin E, vitamin A and other retinoids; and the carotenes such as .beta.-carotene. In practicing this invention, ascorbic acid as anti-oxidant is particularly preferred.

The platelets are separated from the red blood cells and white blood cells of whole blood, primarily through differential centrifugation, although any suitable method for separating platelets from whole blood may be employed in practicing this invention. The overall composition of the invention disclosed herein may contain incidental amounts of white blood cells, due to the fact that the platelets are rarely totally isolated from the other blood components. It is believed that the present invention contains only minimal or trace amounts of white blood cells; it is believed that the white blood cell count of the present invention typically will be below about 3 times 10.sup.7 cell/ml. The bioactive material in the invention is almost exclusively from platelets. The range of the mean platelet volume of the platelets being sequestered is in the range of about 6.6 to 8.4 femtoliters, with an average of about 7.7 femtoliters; this may indicate that the platelets being sequestered are relatively larger or younger than the overall population of platelets.

Activation of growth factors may occur in a variety of manners, by a variety of substances known as activators or agonists. In the invention described herein, said activation results from lysine and the inclusion of an activator or agonist selected from the group consisting of thrombin, glass, collagen, serotonin, adenosine diphosphate (ADP) and acetylcholine (ACH), and combinations thereof. In a particular and preferred version of the invention, said growth factors are included within concentrated platelets, and said activation results from the inclusion of thrombin. One of the important characteristics common to each substance, supporting the inclusion of each in this particular group, is that each such substance is known or believed to enhance cell or tissue growth in addition to the ability to activate platelets. Moreover, said substances, or various combinations thereof, are known or believed to function together in an unexpected synergistic manner to promote wound healing.

The activator or agonist added to the platelet and plasma concentrate is in an amount sufficient to facilitate the formation of the coagulum (gel) having a predetermined viscosity while sufficiently activating growth factors present in the composition. In the preferred case where thrombin is employed as the activator to produce a final soft gel wound composition in a soft gel form, the amount of thrombin generally ranges between about 100 U and about 10,000 U, preferably about 900 U and about 1100 U, most preferably about 1000 U per 10 cc of platelet concentrate. Thrombin is available as Thrombogen.®. thrombin, topical USP (bovine origin) in vials containing 5000 units thrombin (Johnson & Johnson Medical Inc., Arlington, Tex., USA).

Since the admixture of thrombin or other agonists will activate growth factors, the thrombin (or other agonists/activators) should usually be the last substance to be mixed immediately before it is desired that the gelatinous state be set up.

Besides a method of making a wound healant composition, the invention described herein may also include a method of treating a wound, comprising the steps of applying a sufficient amount of a composition of matter comprising growth factors to enhance healing of the wound. Said method of treating a wound may include the use of any of the compositions described herein; it may also include the use of any composition made by any of the methods described herein.

Once applied to a wound, the composition may remain on the wound for as long as 5 days, and perhaps longer depending upon the circumstances such as the location of the wound and other wound characteristics. Although the composition and method described herein are especially useful for the treatment of chronic wounds, they may also be useful in the treatment of acute wounds.

EXAMPLE 1

Preparation of Lyophilized Platelet Rich Plasma for the Use in Wound Healing (Chronic or Acute) and Bone or Tissue Grafts.

(a) The First Method for Human Blood Components Obtained from a Blood Bank or Collection Center:
The Components Needed:
1. Pooled or single donor platelets (containing at least $5 \times 10$ to the $9^{th}$ platelets) about 40 ml to 50 ml per bag.
2. Pooled or single donor fresh frozen plasma (about 250 ml) per bag.
3. Centrifuge with the capabilities of spinning 50 ml tubes up to 5000 rpms.
4. 50 ml tubes.
5. Pipettes from 0.01 ul to 50 ml
6. Vials with stoppers and caps.

Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Thaw the fresh frozen plasma ad insert an amount into the platelet plug container as to cause a platelet count of between 250,000 to 4,500,000 platelets per milliliter. Being very careful that the fresh plasma does not stay thawed for more than 4 hours.
4. Gently rotate back and forth to cause the platelets and plasma to mix well.
5. Pipette the desired amount of PRP into the vials to be lyophilized and place the stoppers in place.
6. Lyophilize at once (take care as to not allow any warming to occur).
7. The first cycle should be for 48 hours.
8. The second cycle should be for 12 hours.

For this example 10 ml of the PRP was Lyophilized and capped.
To Apply to the Wound Using the 10 ml Vials of LPRP:
a. Rehydrate using (10 ml) de-ionized water and allow to stand for at least 10 to 15 minutes.
b. Remove the LPRP using a 20 ml syringe.
c. Add 1 ml of Thrombin (bovine) 1000 u per milliliter
d. Place on the wound and cover with a moist gauze.
e. Cover the wound with an exclusive dressing.
f. Allow too stay in place for 4 to 7 days without changing the dressing.
g. Repeat if necessary.

EXAMPLE 2

(a) The Second Method for Human Blood Components Obtained from a Blood Bank or Collection Center:
The Components Needed:
1. Pooled or single donor platelets (containing at least $5 \times 10$ to the $9^{th}$ platelets) about 40 ml to 50 ml per bag.
2. Pooled or single donor fresh frozen plasma (about 250 ml) per bag.

3. Centrifuge with the capabilities of spinning 50 ml tubes up to 5000 rpms.
4. 50 ml tubes.
5. Pipettes from 0.01 ul to 50 ml
6. Vials with stoppers and caps.
7. GHK-Cu ranging from 0.02 mg/ml to 0.5 mg/ml in liquid form Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Thaw the fresh frozen plasma ad insert an amount into the platelet plug container as to cause a platelet count of between 250,000 to 4,500,000 platelets per milliliter. Being very careful that the fresh plasma does not stay thawed for more than 4 hours.
4. Add an amount of GHK-Cu to equal 1 ml per 9 ml of LPRP
5. Gently rotate back and forth to cause the platelets and plasma to mix well.
6. Pipette the desired amount of PRP into the vials to be lyophilized and place the stoppers in place.
7. Lyophilize at once (take care as to not allow any warming to occur).
8. The first cycle should be for 48 hours.
9. The second cycle should be for 12 hours.

For this example 10 ml of the PRP was Lyophilized and capped.

To Apply to the Wound Using the 10 ml Vials of LPRP:
a. Re-hydrate using (10 ml) de-ionized water and allow to stand for at least 10 to 15 minutes.
b. Remove the LPRP using a 20 ml syringe.
c. Add 1 ml of Thrombin (bovine) 1000 u per milliliter
d. Place on the wound and cover with a moist gauze.
e. Cover the wound with an exclusive dressing.
f. Allow too stay in place for 4 to 7 days without changing the dressing.
g. Repeat if necessary.

(b) The Third Method for Human Blood Components Obtained from a Blood Bank or Collection Center:

The Components Needed:
1. Pooled or single donor platelets (containing at least 5×10 to the $9^{th}$ platelets) about 40 ml to 50 ml per bag.
2. Pooled or single donor fresh frozen plasma (about 250 ml) per bag.
3. Centrifuge with the capabilities of spinning 50 ml tubes up to 5000 rpms.
4. 50 ml tubes.
5. Pipettes from 0.01 ul to 50 ml
6. Vials with stoppers and caps.
7. GHK-Cu ranging from 0.02 mg/ml to 0.5 mg/ml gauze.

Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Thaw the fresh frozen plasma ad insert an amount into the platelet plug container as to cause a platelet count of between 250,000 to 4,500,000 platelets per milliliter. Being very careful that the fresh plasma does not stay thawed for more than 4 hours.
4. Gently rotate back and forth to cause the platelets and plasma to mix well.
5. Pipette the desired amount of PRP into the vials to be lyophilized and place the stoppers in place.
6. Lyophilize at once (take care as to not allow any warming to occur).
7. The first cycle should be for 48 hours.
8. The second cycle should be for 12 hours.

For this example 10 ml of the PRP was Lyophilized and capped.

To Apply to the Wound Using the 10 ml Vials of LPRP:
a. Re-hydrate using (10 ml) de-ionized water and allow to stand for at least 10 to 15 minutes.
b. Remove the LPRP using a 20 ml syringe.
c. Add 1 ml of Thrombin (bovine) 1000 u per milliliter
d. Place on the wound and cover with GHK-Cu gauze.
e. Cover the wound with an exclusive dressing.
f. Allow too stay in place for 4 to 7 days without changing the dressing.
g. Repeat if necessary.

(c) The Forth Method for Human blood components obtained from a blood bank or collection center:

The Components Needed:
1. Pooled or single donor platelets (containing at least 5×10 to the $9^{th}$ platelets) about 40 ml to 50 ml per bag.
2. Pooled or single donor fresh frozen plasma (about 250 ml) per bag.
3. Centrifuge with the capabilities of spinning 50 ml tubes up to 5000 rpms.
4. 50 ml tubes.
5. Pipettes from 0.1 ul to 50 ml
6. Vials with stoppers and caps.
7. Vitamin C is an amount equal to 10%

Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Thaw the fresh frozen plasma ad insert an amount into the platelet plug container as to cause a platelet count of between 250,000 to 4,500,000 platelets per milliliter. Being very careful that the fresh plasma does not stay thawed for more than 4 hours.
4. Add an amount of Vitamin C to equal 1 ml per 9 ml of LPRP
5. Gently rotate back and forth to cause the platelets and plasma to mix well.
6. Pipette the desired amount of PRP into the vials to be lyophilized and place the stoppers in place.
7. Lyophilize at once (take care as to not allow any warming to occur).
8. The first cycle should be for 48 hours.
9. The second cycle should be for 12 hours.

For this example 10 ml of the PRP was Lyophilized and capped.

To Apply to the Wound Using the 10 ml Vials of LPRP:
a. Re-hydrate using (10 ml) de-ionized water and allow to stand for at least 10 to 15 minutes.
b. Remove the LPRP using a 20 ml syringe.
c. Add 1 ml of Thrombin (bovine) 1000 u per milliliter
d. Place on the wound and cover with a moist gauze.
e. Cover the wound with an exclusive dressing.
f. Allow too stay in place for 4 to 7 days without changing the dressing.
g. Repeat if necessary.

(d) The Fifth Method for Human Blood Components Obtained from a Blood Bank or Collection Center:
The Components Needed:
1. Pooled or single donor platelets (containing at least 5×10 to the $9^{th}$ platelets) about 40 ml to 50 ml per bag.
2. Pooled or single donor fresh frozen plasma (about 250 ml) per bag.
3. Centrifuge with the capabilities of spinning 50 ml tubes up to 5000 rpms.
4. 50 ml tubes.
5. Pipettes from 0.01 ul to 50 ml
6. Vials with stoppers and caps.
7. Vitamin C is an amount equal to 10%

Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Thaw the fresh frozen plasma ad insert an amount into the platelet plug container as to cause a platelet count of between 250,000 to 4,500,000 platelets per milliliter. Being very careful that the fresh plasma does not stay thawed for more than 4 hours.
4. Gently rotate back and forth to cause the platelets and plasma to mix well.
5. Pipette the desired amount of PRP into the vials to be lyophilized and place the stoppers in place.
6. Lyophilize at once (take care as to not allow any warming to occur).
7. The first cycle should be for 48 hours.
8. The second cycle should be for 12 hours.

For this example 10 ml of the PRP was Lyophilized and capped.
To Apply to the Wound Using the 10 ml Vials of LPRP:
 a. Re-hydrate using (10 ml) de-ionized water and allow to stand for at least 10 to 15 minutes.
 b. Remove the LPRP using a 20 ml syringe.
 c. Add 1 ml of Thrombin (bovine) 1000 u per milliliter
 d. Add 1 ml of 10% Vitamin C, A.K.A. (Ascorbic Acid)
 e. Place on the wound and cover with a moist gauze.
 f. Cover the wound with an exclusive dressing.
 g. Allow too stay in place for 4 to 7 days without changing the dressing.
 h. Repeat if necessary.

(e) The Sixth Method for Human Blood Components Obtained from a Blood Bank or Collection Center:
The Components Needed:
1. Pooled or single donor platelets (containing at least 5×10 to the $9^{th}$ platelets) about 40 ml to 50 ml per bag.
2. Pooled or single donor fresh frozen plasma (about 250 ml) per bag.
3. Centrifuge with the capabilities of spinning 50 ml tubes up to 5000 rpms.
4. 50 ml tubes.
5. Pipettes from 0.01 ul to 50 ml
6. Vials with stoppers and caps.
7. Vitamin C is an amount equal to 10%
8. GHK-Cu ranging from 0.02 mg/ml to 0.5 mg/ml in liquid form Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Thaw the fresh frozen plasma ad insert an amount into the platelet plug container as to cause a platelet count of between 250,000 to 4,500,000 platelets per milliliter. Being very careful that the fresh plasma does not stay thawed for more than 4 hours.
4. Add an amount of Vitamin C to equal 0.05 ml to 1 ml per 9 ml of LPRP
5. Add an amount of GHK-Cu to equal 0.05 ml to 1 ml per 9 ml of LPRP
6. Gently rotate back and forth to cause the platelets and plasma to mix well.
7. Pipette the desired amount of PRP into the vials to be lyophilized and place the stoppers in place.
8. Lyophilize at once (take care as to not allow any warming to occur).
9. The first cycle should be for 48 hours.
10. The second cycle should be for 12 hours.

For this example 10 ml of the PRP was Lyophilized and capped.
To Apply to the Wound Using the 10 ml Vials of LPRP:
 a. Re-hydrate using (10 ml) de-ionized water and allow to stand for at least 10 to 15 minutes.
 b. Remove the LPRP using a 20 ml syringe.
 c. Add 1 ml of Thrombin (bovine) 1000 u per milliliter
 d. Place on the wound and cover with a moist gauze.
 e. Cover the wound with an exclusive dressing.
 f. Allow too stay in place for 4 to 7 days without changing the dressing.
 g. Repeat if necessary.

EXAMPLE 3

(a) The Sixth Method for Human or Animal, Obtained from Apheresis Either Autologous or Homologous:
The Components Needed:
1. Single donor platelets (obtained from apheresis) about 40 ml to 50 ml per bag.
2. Centrifuge with the capabilities of spinning 50 ml tubes up to 5000 rpms.
3. 50 ml tubes.
4. Pipettes from 0.01 ul to 50 ml.
5. Vials with stoppers and caps.

Method:
1. Remove the platelets from the bag of apheresis platelets.
2. Add fresh plasma into the platelets in an amount to cause a platelet count of between 250,000 to 4,500,000 platelets per milliliter. Being very careful that the fresh platelet rich plasma does not stay thawed for more than 6 hours.
3. Gently rotate back and forth to cause the platelets and plasma to mix well.
4. Pipette the desired amount of PRP into the vials to be lyophilized and place the stoppers in place.
5. Lyophilize at once (take care as to not allow any warming to occur).
6. The first cycle should be for 48 hours.
7. The second cycle should be for 12 hours.

For this example 10 ml of the PRP was Lyophilized and capped.
To Apply to the Wound Using the 10 ml Vials of LPRP:
 a. Re-hydrate using (10 ml) de-ionized water and allow to stand for at least 10 to 15 minutes.
 b. Remove the LPRP using a 20 ml syringe.
 c. Add 1 ml of Thrombin (bovine) 1000 u per milliliter
 d. Place on the wound and cover with a moist gauze.
 e. Cover the wound with an exclusive dressing.

f. Allow too stay in place for 4 to 7 days without changing the dressing.
g. Repeat if necessary.

EXAMPLE 4

(c) The Third Method for Human Blood Components Obtained from a Blood Bank and Activated Prior to Lyophilization with Thrombin (Bovine or Intrinsic):

The Components Needed:
1. Pooled or single donor platelets (containing at least $5 \times 10$ to the $9^{th}$ platelets) about 40 ml to 50 ml per bag.
2. Pooled or single donor fresh frozen plasma (about 250 ml) per bag.
3. Centrifuge with the capabilities of spinning 50 ml tubes up to 5000 rpms.
4. 50 ml tubes.
5. Pipettes from 0.01 ul to 50 ml Vials with stoppers and caps.
6. Thrombin and Calcium Chloride or Glass Beads or Glass Wool.

Method:
1. Remove the platelets from the bag and place in a 50 ml tube and centrifuge for 15-20 min. at 5000 rpms to form a platelet plug, which is known in the art.
2. Remove and discard the platelet poor plasma from the tube of platelets.
3. Remove 50% of the platelet plug and activate the plug with Thrombin or pass the platelets through either glass wool or glass beads and allow activated platelets to rest for about 15 min. then centrifuge for 15 min. and remove the serum with out the plug. Then pipette equal amounts of the serum into the vials in equal amounts.
4. Thaw the fresh frozen plasma and insert an amount into the platelet plug container as to cause a platelet count of between 250,000 to 4,500,000 platelets per milliliter. Being very careful that the fresh plasma does not stay thawed for more than 4 hours.
5. Gently rotate back and forth to cause the platelets and plasma to mix well.
6. Pipette the desired amount of PRP into the vials to be lyophilized and place the stoppers in place.
7. Lyophilize at once (take care as to not allow any warming to occur).
8. The first cycle should be for 48 hours.
9. The second cycle should be for 12 hours.

For this example 10 ml of the PRP was Lyophilized and capped.

To Apply to the Wound Using the 10 ml Vials of ALPRP:
h. Rehydrate using (10 ml) de-ionized water and allow to stand for at least 10 to 15 minutes.
i. Remove the LPRP using a 20 ml syringe.
j. Place on the wound and cover with a moist gauze.
k. Cover the wound with an exclusive dressing.
l. Allow too stay in place for 4 to 7 days without changing the dressing.
m. Repeat if necessary.

What is claimed:

1. A process for preparing platelet rich plasma to obtain growth factors for use in wound healing comprising:
providing platelets selected from one of a pooled and a single donor platelet source;
concentrating said platelets into a platelet rich plasma;
discarding platelet poor plasma from said platelet rich plasma following concentration of said platelet rich plasma;
adding fresh plasma into said platelet rich plasma;
mixing said platelet rich plasma with said fresh plasma to provide a platelet rich plasma mixture;
starting lyophilization of said platelet rich plasma mixture immediately following mixing while said platelet rich plasma mixture is still in liquid form to nonchemically release growth factors from said platelet rich plasma under lyophilization conditions that do not activate the platelets; and
continuing lyophilization until a freeze-dried composition results.

2. The process according to claim 1 including the step of re-hydrating said lyophilized platelet rich plasma using de-ionized water.

3. The process according to claim 2 including the step of re-hydrating said platelet rich plasma mixture for a period of 10-15 minutes.

4. The process according to claim 2 including the step of recovering said lyophilized platelet rich plasma following re-hydration.

5. The process according to claim 4 including the step of activating said lyophilized platelet rich plasma for placement on a wound.

6. The process according to claim 5 including the step of adding thrombin to said lyophilized platelet rich plasma.

7. The process according to claim 6 including the step of prior to mixing said thrombin, mixing at least one antibiotic in sufficient amount(s) to reduce infection by bacteria.

8. The process according to claim 7 including the step of selecting said antibiotic from the group consisting of an antibiotic that is at least bacteriocidal to *Pseudomonas* and *Klebsella* bacteria.

9. The process according to claim 8 including the step of selecting said antibiotic from the group consisting neosporin, vancomycin and gentamycin, and combinations thereof.

10. The process according to claim 1 including the step of either prior to or after lyophilization of said platelet rich plasma mixture adding at least one retinoid in sufficient amount(s) to further enhance wound healing.

11. The process according to claim 1 including the step of prior to or after lyophilization, admixing, in therapeutically effective amount(s), concentrated platelets, ascorbic acid, at least one retinoid and at least one antibiotic bacteriocidal to at least *Pseudomonas* and *Klebsella* bacteria.

* * * * *